(12) United States Patent
McCarron et al.

(10) Patent No.: US 6,498,046 B2
(45) Date of Patent: Dec. 24, 2002

(54) INFRARED THERMOGRAPHIC SCREENING TECHNIQUE FOR SEMICONDUCTOR-BASED CHEMICAL SENSORS

(75) Inventors: Eugene Michael McCarron, Greenville, DE (US); Patricia A. Morris, Montchanin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/978,129

(22) Filed: Oct. 16, 2001

(65) Prior Publication Data

US 2002/0106827 A1 Aug. 8, 2002

Related U.S. Application Data

(60) Provisional application No. 60/240,620, filed on Oct. 16, 2000.

(51) Int. Cl.[7] .............................................. H01L 21/00
(52) U.S. Cl. ........................................................ 438/10
(58) Field of Search ............................... 438/10, 14, 17

(56) References Cited

U.S. PATENT DOCUMENTS

| | | |
|---|---|---|
| 4,007,435 A | 2/1977 | Tien |
| 4,151,503 A | 4/1979 | Cermak et al. |
| 4,225,842 A | 9/1980 | Schleselman et al. |
| 4,234,542 A | 11/1980 | Romine |
| 4,387,359 A | 6/1983 | Tien et al. |
| 4,535,316 A | 8/1985 | Wertheimer et al. |
| 4,542,640 A | 9/1985 | Clifford |
| 4,646,009 A * | 2/1987 | Mallory ...................... 324/158 |
| 4,770,760 A | 9/1988 | Noda et al. |
| 5,239,483 A | 8/1993 | Weir |
| 5,554,273 A | 9/1996 | Demmin et al. |
| 5,630,920 A | 5/1997 | Friese et al. |
| 5,683,569 A * | 11/1997 | Chung et al. ................ 205/775 |
| 5,731,510 A | 3/1998 | Jones et al. |
| 5,736,028 A | 4/1998 | Hjortsberg et al. |
| 5,776,601 A | 7/1998 | Fournier et al. |
| 5,879,526 A | 3/1999 | Dietz et al. |
| 6,012,282 A | 1/2000 | Kato et al. |
| 6,082,176 A | 7/2000 | Kondo et al. |
| 6,084,418 A | 7/2000 | Takami et al. |
| 6,085,576 A | 7/2000 | Sunshine et al. |
| 6,235,243 B1 | 5/2001 | Fleischer et al. |
| 6,315,574 B1 * | 11/2001 | Kamieniecki et al. ........ 439/16 |

FOREIGN PATENT DOCUMENTS

| | | |
|---|---|---|
| DE | 4408361 | 9/1995 |
| DE | 4408504 | 9/1995 |
| WO | WO0000808 | 1/2000 |

OTHER PUBLICATIONS

S.W. Moore, et al., A modified multilayer perceptron model for gas mixture analysis, Sensors and Actuators B, 15–16 (1993) pp. 344–348, Elsevier Sequoia.

(List continued on next page.)

Primary Examiner—David Nelms
Assistant Examiner—Quoc Hoang

(57) ABSTRACT

An infrared thermographic technique for rapid parallel screening of compositional arrays of potential chemical sensor materials has been developed. The technique involves applying a voltage bias and the associated current to the sample array during screening. The thermographic response is amplified by the resistance change that occurs with gas adsorption, and is directly monitored as the temperature change associated with $I^2R$ heating. This technique can also be used to determine n- or p-type character for the semiconductor in question.

17 Claims, 9 Drawing Sheets

OTHER PUBLICATIONS

H. Meixner, et al., Metal oxide sensors, Sensors and Actuators B 33 (1996) pp. 198–202, Elsevier Science.

J. Getino, et al., Integrated sensor array for gas analysis in combustion atmospheres, Sensors and Actuators B 33 (1996) pp. 128–133, Elsevier Science.

Corrado Di Natale, et al., Study of the effect of the sensor operating temperature on $SnO_2$–based sensor–array performance, Sensors and Actuators B 23 (1995) pp. 187–191, Elsevier Science.

Brent T. Marquis, et al., A semiconducting metal oxide sensor array for the detection of $NO_x$ and $NH_3$, Sensors and Actuators B 77 (2001) pp. 100–110, Elsevier Science.

G. Huyberechts, et al., Simultaneous quantification of carbon monoxide and methane in humid air using a sensor array and an artificial neural network, Sensors and Actuators B 45 (1997) pp. 123–130, Elsevier Science.

Kazimierz Brudzewski, et al., Gas analysis system composed of a solid–state sensor array and hybrid neural network structure, Sensors and Actuators B 55 (1999) pp. 38–46, Elsevier Science.

P.C. Jurs, et al., Computational methods for the analysis of chemical sensor array data from volatile analytes, Chem Rev. 2000, 100, pp. 2649–2678, American Chemical Society.

Keith J. Albert, et al., Cross–reactive chemical sensor arrays, Chem. Rev. 2000, 100, pp. 2595–2626, American Chemical Society.

P. Vincenzini, et al., Solid state chemical and biochemical sensors, Advances in Science and Technology, 26, pp. 335–345, National Research Center, Italy.

Antonio Parado, et al., Nonlinear inverse dynamic models of gas sensing systems based on chemical sensor arrays for quantitative measurements, IEEE Transactions on Instrumentation and Measurement, vol. 47, No. 3, Jun. 1998, pp. 644–651.

BS Hoffheins, et al., Performance of simplified chemical sensor arrays in a neural network–based analytical instrument, Analysis (1992) 20, pages 201–207, Elsevier, Paris.

Corrado Di Natale, et al., Performance evaluation of an $SnO_2$–based sensor array for the quantitative measurement of mixtures of $H_2S$ and $NO_2$, Sensors and Actuators B, 20 (1994) pp. 217–224.

H. Meixner, et al., Chemosensors for motor management systems of the future, Fresenius J. Anal Chem. (1994) 348, pp. 536–541.

* cited by examiner gold on Al$_2$O$_3$     dielectric layer     sensor array

Compositional Map of Sample Array

1% Butane

INFRARED THERMOGRAPHIC SCREENING TECHNIQUE FOR SEMICONDUCTOR-BASED CHEMICAL SENSORS

This application claims the benefit of the filing date of U.S. Provisional Application No. 60/240,620, filed Oct. 16, 2000.

FIELD OF THE INVENTION

The invention is directed towards a method of screening semiconductor materials for use as chemical sensors, and a method to determine the conductivity type of semiconductors.

BACKGROUND OF THE INVENTION

The need for chemical sensors capable of detecting gases such as nitrogen oxides, hydrocarbons, carbon monoxide and oxygen at the ppm to the percent level is longstanding. These sensors can be used in many applications, such as automotive exhaust sensing, or detection of toxic atmospheres. Taguchi, or semiconducting resistance-type, sensors are seen as the most likely candidates for these types of applications. Of particular value are semiconducting metal oxides whose electrical resistance varies with the composition of the surrounding gaseous atmosphere. To date only a very limited number of semiconducting compositions have been examined. Thus there is a further need to develop a rapid parallel screening technique for candidate materials.

In semiconducting materials, conduction of electricity is explained in terms of majority and minority carriers of electric charge. In n-type semiconductors, electrons are the majority carriers and holes, i.e. the spaces left by electrons, are the minority carriers. In p-type semiconductors the opposite is true; the holes are the majority carriers and the electrons are the minority carriers.

Previously researchers have used the "hot probe" technique to measure p- or n-type. Another test for p- or n-type involves forming a contact diode with a wafer by means of a probe. The direction of current flow, either d.c. or a.c., through the diode indicates conduction type. Both of these methods are slow and use expensive, bulky equipment. They are also not suitable for rapid, parallel methods of screening for large numbers of materials.

SUMMARY OF THE INVENTION

Disclosed is a method for determining the change in resistance of a semiconducting material in response to exposure to a sample gas by: a) applying a voltage bias across the semiconducting material; b) measuring the difference between the temperature of the material as exposed to said sample gas and the temperature of the material as exposed to a reference gas; and c) relating the measured difference in temperature to a change in resistance. The voltage bias is preferably about 0.5 V to about 200 V, and the difference in the temperature is preferably measured with an infrared thermographic measuring system. The semiconducting material is preferably a metal oxide deposited on a solid substrate.

Also disclosed is a method for parallel screening of semiconducting materials for suitability as chemical sensing materials by determining the resistance change in a plurality of semiconducting materials in response to a sample gas by: a) applying a voltage bias across each semiconducting material; b) simultaneously measuring the difference between the temperature of each material as exposed to said sample gas and the temperature of each material as exposed to a reference gas; and c) relating the measured difference in temperature for each material to a change in resistance of that material.

Also disclosed is a method for the parallel screening of a plurality of semiconducting materials for suitability as chemical sensing materials by:
  a) applying a voltage bias across each semiconducting material;
  b) simultaneously measuring the difference between the temperature of each material as exposed to a sample gas and the temperature of each material as exposed to a reference gas; and
  c) comparing the measured difference in temperature exhibited by a first material to the measured difference in temperature exhibited by a second material.

Also disclosed is a method for determining the conductivity-type of a semiconducting material by: a) applying a voltage bias across the semiconducting material; b) measuring the difference between the temperature of the material as exposed to a sample gas and the temperature of the material as exposed to a reference gas; and c) relating the measured difference in temperature to a conductivity type.

DETAILED DESCRIPTION OF THE INVENTION

Figure 1:
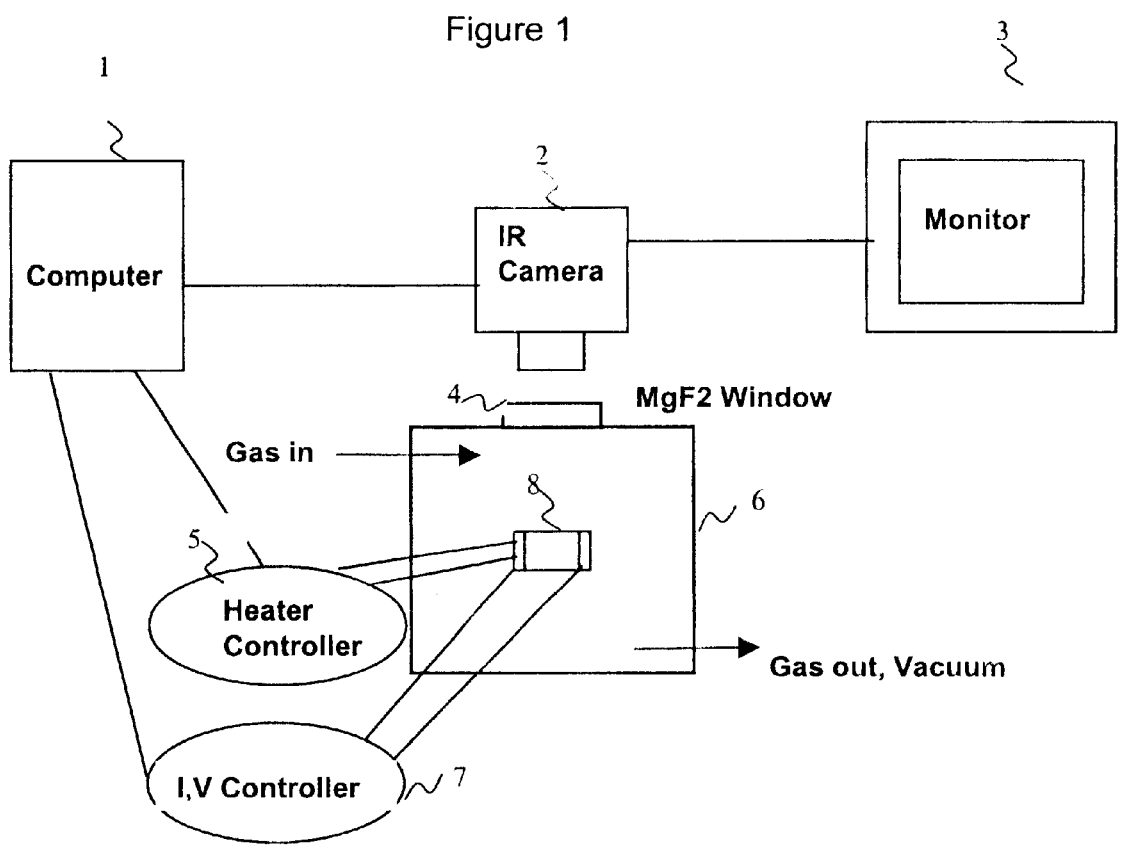
FIG. 1 is a schematic of the testing apparatus.

The invention is directed to a method to monitor and measure the change in the interaction between a semiconducting sensor candidate and a variety of sample gases and gas mixtures of interest relative to a reference gas. The choice of reference gas is limited essentially only by safety considerations and the chemical compatibility of the particular gas systems being used. The reference gas may be chosen from a variety of inert gases. Particular examples of potential reference gases may include air, $CO_2$, argon, neon, helium, oxygen or nitrogen. Mixtures of oxygen and nitrogen, such as 2% $O_2$/98% $N_2$, have been found useful.

The technique involves the use of an applied voltage (V) bias and current (I) across the individual sensor candidates, or sample material, to screen the materials. The resistance of a semiconductor can change when exposed to a gas, depending on the chemistry of that particular gas, especially if the gas is an electron donor gas or an electron acceptor gas.

Thus, the change in the resistance (R) of a semiconductor sample, which is sensitive to a specific gas, can be related to the observed temperature change of the sample in terms of the associated $I^2R$ heating. The temperature behavior of a candidate material in a sample gas can be related to the temperature behavior of the material in a reference gas for the purpose of indicating change in resistance or conductivity type.

The semiconducting material can be of any type, but especially useful are metal oxides such as $ZnO$, $TiO_2$, $WO_3$ and $SnO_2$. The semiconducting material can be a mixture of a semiconducting material with other semiconducting materials, or with any inorganic material, or combinations thereof. The semiconducting materials of interest can be deposited on a suitable solid substrate that is an insulator such as, but not limited to, alumina or silica. A voltage bias is applied across the semiconducting material. The magnitude of the voltage bias in the range of about 0.5 to about 200 V is suitable. Preferred is 10 V.

Any method of depositing the semiconducting material to the substrate and applying the voltage bias is suitable. One technique used for deposition is applying the semiconducting material on an alumina substrate on which interdigitated gold electrodes are screen printed. The semiconducting material can be deposited on top of gold electrodes by hand painting semiconductor materials on the substrate, nanopipetting materials into wells, or thin film deposition techniques. Most techniques are followed by a final firing to sinter the semiconducting materials.

The gas of interest to which the semiconducting material will be exposed (the sample gas) can be a single gas, a mixture, or one or more gases mixed with an inert gas such as nitrogen. Particular gases of interest are donor and acceptor gases. These are gases that either donate electrons to the semiconducting material, such as carbon monoxide, $H_2S$ and hydrocarbons; or accept electrons from the semiconducting material, such as $O_2$, nitrogen oxides (commonly depicted as $NO_x$), and halogens. When exposed to a donor gas, n-type semiconducting materials will have a decrease in resistivity, increasing the current, and will therefore show an increase in temperature due to $I^2R$ heating. When exposed to an acceptor gas, n-type semiconducting materials will have an increase in resistivity, decreasing the current and therefore will show a decrease in temperature due to $I^2R$ heating. The opposite occurs with p-type semiconducting materials.

The temperature change can be recorded using any suitable means. One preferred method is the use of an infrared camera to record IR thermographic images. A false color scale visually and vividly depicts the temperature changes, although a gray scale could also be used. Background readings using an inert gas such as $N_2$ can be subtracted for more accuracy. The observed temperature changes relate to the sensitivity of the semiconducting materials to the particular gas to which the material is exposed.

The temperatures, gas concentration, thickness of material, and voltages used can vary and depend on the sensitivity expected of the material. In general, response increases with higher temperatures, thicker materials, higher surface area, and voltage.

The instant invention is also directed to a method for the parallel screening of multiple semiconducting materials. An array or library of semiconducting materials can be screened simultaneously using an infrared camera, quickly and easily depicting the response of each material to the gas of interest. The array of candidate materials is exposed simultaneously to the sample gas, whereupon temperature is evaluated; and the array of candidate materials is exposed simultaneously to the reference gas, whereupon temperature is evaluated. Exposure of the array to the sample gas may occur before or after exposure to the reference gas.

Another aspect of the invention is a method to determine the n-type or p-type conductivity of the semiconducting materials. As described above, the direction of the temperature change when a semiconducting material is exposed to either a donor gas or an acceptor gas will indicate whether the semiconducting material is a p-type or n-type semiconductor. Correlating the types of gases used as the sample and reference gases with the temperature response will accurately define the conductivity type. This method can also be used as described above to characterize an array or library of semiconducting materials.

EXAMPLES

Figure 2:
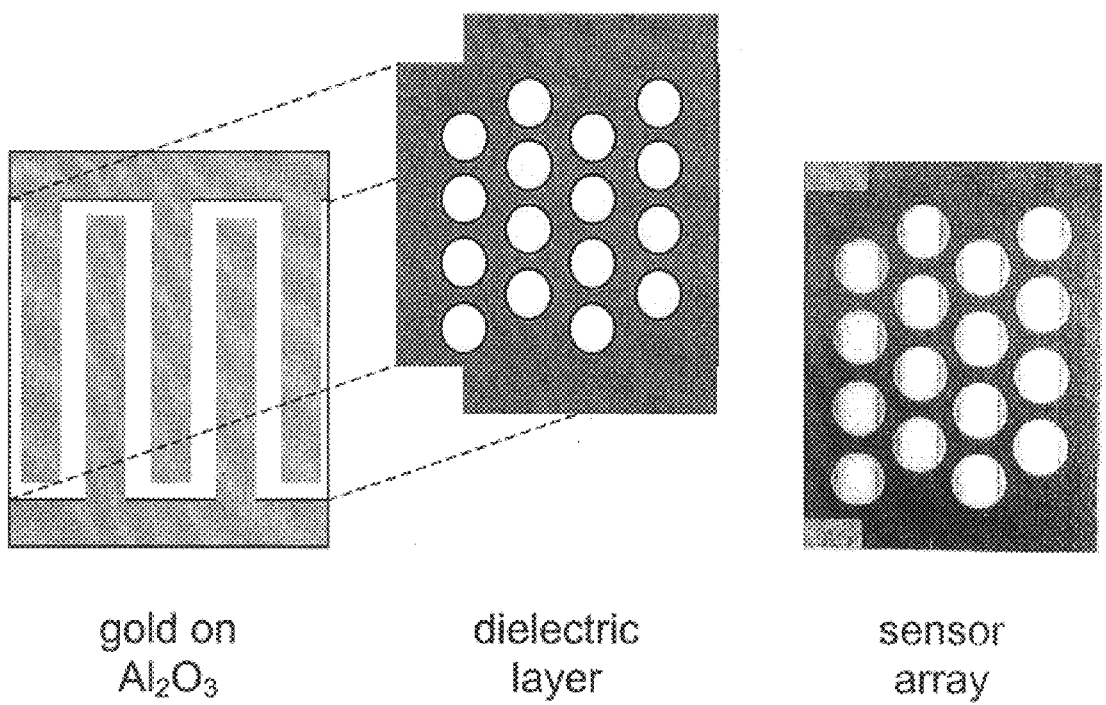
FIG. 2 is a schematic of the pattern of interdigitated electrodes overlaid with the dielectric overlayer, forming the sixteen blank wells.

The following non-limiting examples will illustrate the invention but are not intended to limit it in any way. The following definitions are used herein:

BET Brunauer-Emmett-Teller
I Current
IR Infrared
mA Milli-amperes
$NO_x$ Nitrogen oxides mixture
R Resistance
sccm Standard cubic centimeters per minute
V Voltage Sixteen-well arrays were made as follows. First a pattern of interdigitated electrodes pattern was screen printed on an alumina substrate (CoorsTek 96% alumina, 1"×¾"×0.025" thick) using a gold conductor paste (DuPont iTechnologies Paste Product #5715). The gold conductor lines were formed by firing the part in a 10-zone belt furnace with a cycle time of 30 minutes and a peak temperature of 850° C. Following the electrode preparation, a second screen printing of a dielectric overlayer (DuPont iTechnologies Paste Product #5704) was done, which when fired, formed the sixteen blank wells and the corner contact pads for hook-up to the I, V power supply which controlled the current and voltage. FIG. 2 depicts a schematic of the interdigitated electrodes pattern overlaid with the dielectric overlayer, forming the sixteen blank wells. The arrays were made by hand painting individual semiconductor material pastes into each well (see FIG. 3). The pastes were comprised of the appropriate amount of −325 mesh semiconductor powder, medium (DuPont iTechnologies M2619), and surfactant (DuPont iTechnologies R0546). The medium and surfactant were first mixed together and the semiconductor powder added in steps to ensure proper wetting. Optionally, solvent (DuPont iTechnologies R4553) was added for viscosity purposes. The paste was then transferred to an agate mortar and ground for more thorough mixing. Using a finely pointed wooden applicator, a very small amount of paste was placed into one of the wells of the array. Once all the wells were filled with the various pastes the part was dried at 120° C. for 10 minutes. Firing was done using a Fisher programmable box furnace with a 1°/min-ramp rate up to 650° C., a 30-minute hold at 650° C., and then a 5°/min-ramp rate down to room temperature.

Next, leads were attached to the contact pads. A 0.005" platinum wire was attached to each of the two open pads on the test array using SEM Au paste (Pelco Company, Catalog #16023). The part was dried at 120° C. for at least four hours before connecting it to the power supply.

FIG. 1 depicts the apparatus used for all Examples. The test chamber 6 consisted of a 2.75" cube containing input and output valves for gas flow, two thermocouple feed-throughs, two electrical feed-throughs, and a 1" $MgF_2$ window 4. All gases and gas mixtures were introduced into this controlled atmosphere chamber via an automated multi-gas handling system (MKS model #647B). The electrical feed-throughs provided connections to a sample heater (Advanced Ceramics, Boralectric heater #HT-42) located under the sample array chip 8 and a voltage/current power supply 7 (Keithley Instruments model #236). The sample heater was controlled using a unit 5 from Hampton Controls (70VAC/700W phase angle). The sample array was imaged through the infrared transparent $MgF_2$ window with the infrared camera 2 (Inframetrics PM390) focused on the front surface of the array chip using a 100 $\mu$m close-up lens. The infrared camera detects radiation between 3.4–5 $\mu$m. The temperature measurement range for this instrument is –10 to 1500° C. with an accuracy of 2° C. and a sensitivity of 0.1° C. The camera, heater control, power supply, and camera were monitored and controlled via computer 1 and monitor 3.

Prior to screening, the sample array was placed inside the test chamber on top of the sample heater, capable of heating the array from room temperature to approximately 800° C. The lead wires from the array were then connected to the electrical feed-through which was connected to the voltage/current power supply unit. The chamber was closed and placed in the visual path of the infrared (IR) camera. Artificial air (100 sccm $N_2$, 25 sccm $O_2$) was then allowed to flow into the chamber prior to heating the sample. Next, the sample was heated at approximately 10° C./minute to the desired temperature and equilibrated before the voltage/current power supply unit was turned on and a voltage applied. The voltage was typically adjusted to allow a current flow array of between 10–20 mA through the sample array.

Unless otherwise noted, the content of all gas mixtures described below is stated in percent by volume.

IR thermographic images of the array of materials were taken 20 minutes after each change in the gas composition to allow for equilibration to the new set of conditions. The temperatures of the materials in 98% $N_2$–2% $O_2$ reference gas were subtracted from each example in order to determine the temperature signals. Examples shown use a gray scale to depict temperature changes, although a false color scale was also used. ThermMonitor 95 Pro, version 1.61 (Thermoteknix Systems, Ltd.) was used for the temperature subtractions. A CoO emissivity reference pad ($\epsilon$=0.9) was used to determine the temperature of the sample array.

Figure 3:
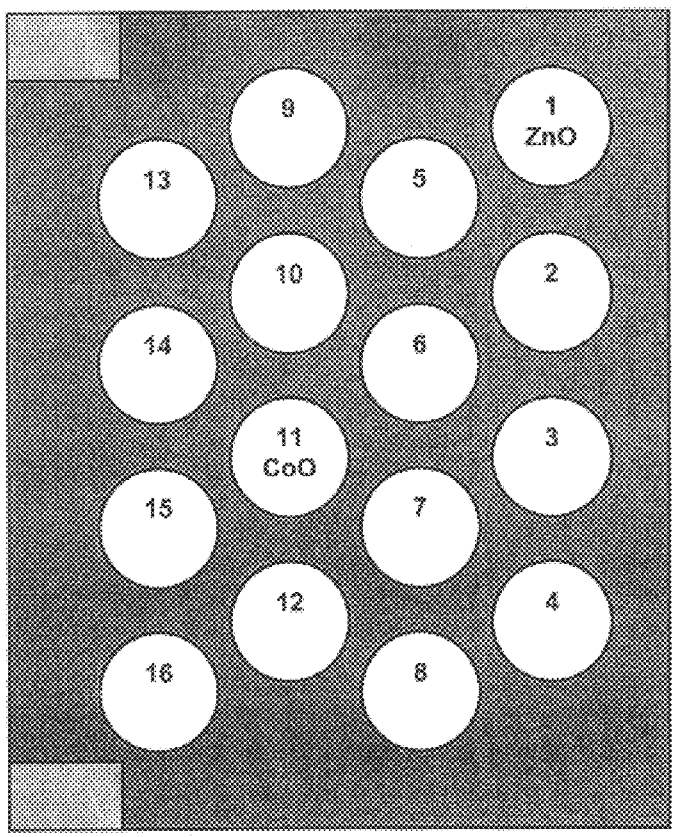
FIG. 3 is a compositional map of the sample array used in the examples.

The sample array used for Examples 2–5 is shown in FIG. 3, with positions of individual compounds and the CoO reference indicated.

Example 1
Effect of Voltage

Figure 4:
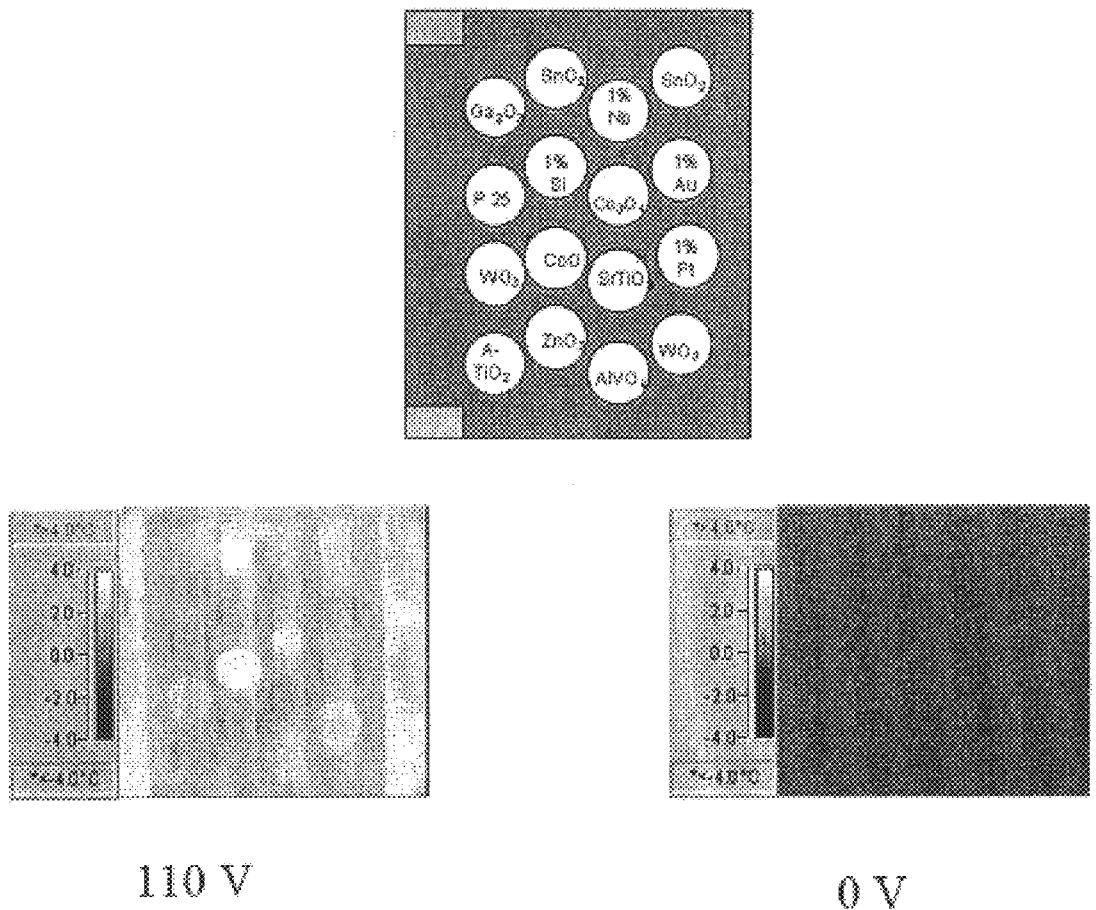
FIG. 4 is the thermographic images of a sample array depicting the effect of voltage, and the corresponding composition map.

The utility of the voltage-enhanced IR technique was demonstrated in FIG. 4. FIG. 4 shows subtracted images of the response of an n-type semiconductor array to the target gas (1% CO in $N_2$) minus the reference gas (2% $O_2$ in $N_2$) at room temperature, both with and without an applied voltage. With an applied voltage, the change in gas environment was observed to cause a positive and persistent heat signature for a number of the semiconductor pads. In particular, for n-type semiconductors, the change from an acceptor ($O_2$) to a donor (CO) gas resulted in a decrease in resistivity (i.e., electrons added to the conduction band) and hence an increase in current. Thus, a positive heat signature was detected due to the dominant power term associated with $I^2R$ heating. Conversely, in the absence of an applied voltage, the only temperature change that could be expected would be due to the transient heat associated with differential gas absorption. Since the heats of adsorption are typically small no effect in the absence of a voltage was seen.

Example 2
Effect of Donor and Acceptor Gases

Figure 5:
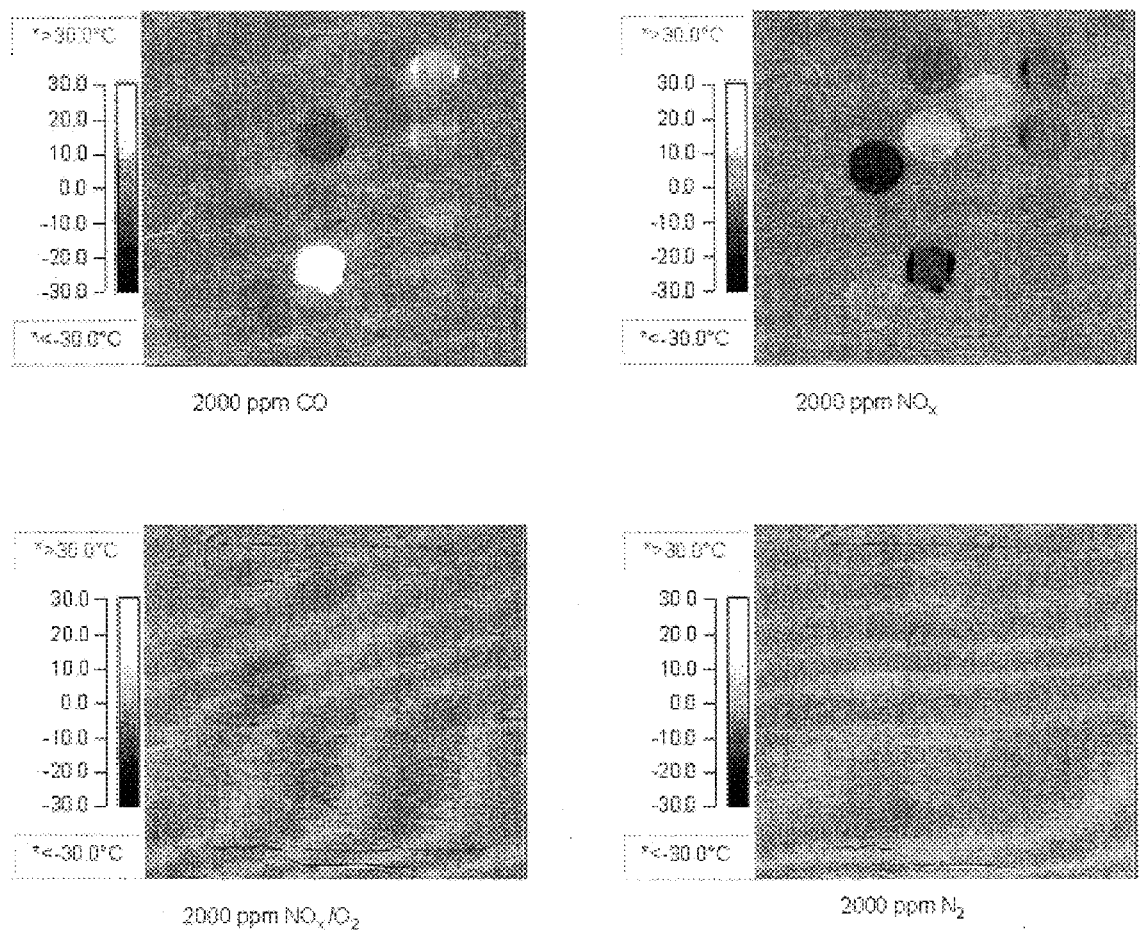
FIG. 5 is the thermographic images of a sample array exposed to CO, $NO_x$, and $O_2$ at 450° C.
Figure 6:
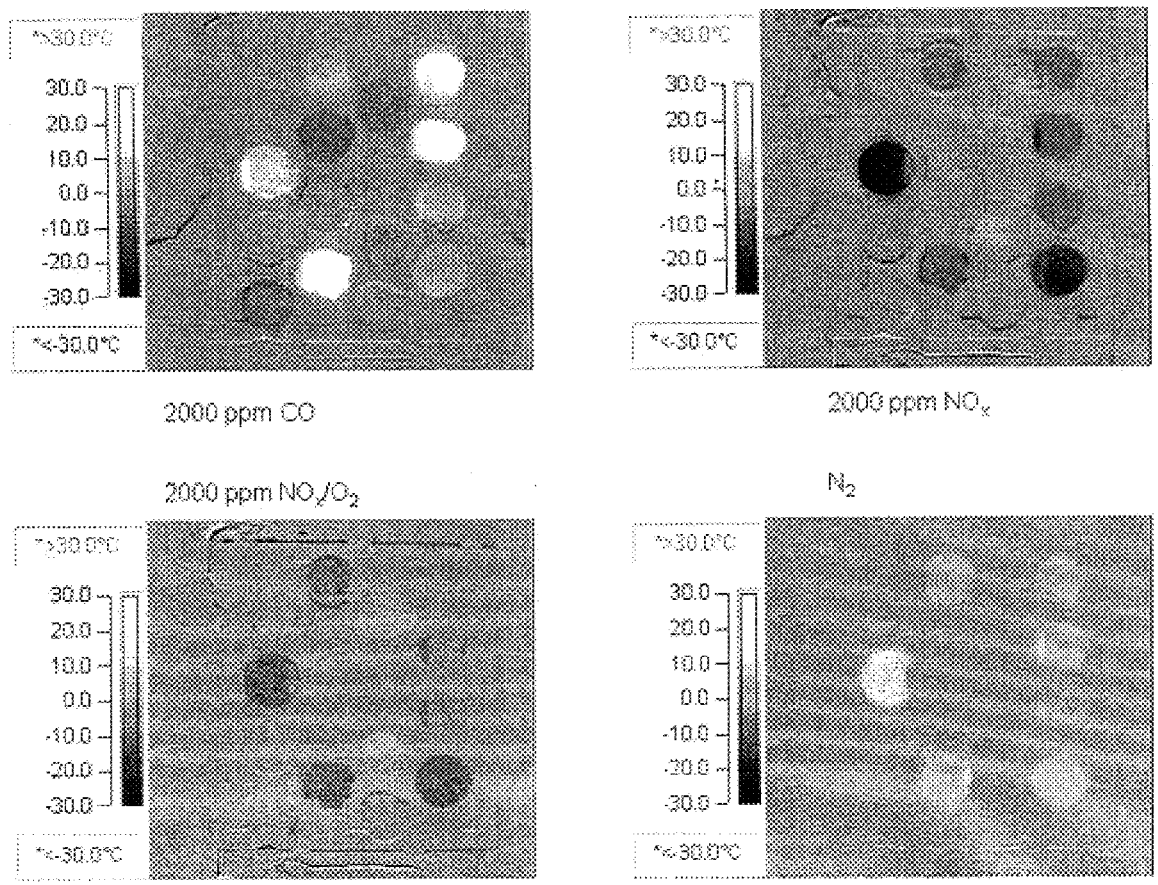
FIG. 6 is the thermographic images of a sample array exposed to CO, $NO_x$, and $O_2$ at 600° C.

Absolute temperature changes ranging from +33.2 to –9.1° C. were observed for certain materials upon changing the atmosphere from donor gases (such as 2000 ppm CO or 1% butane) to acceptor gases (such as 2000 ppm $NO_x$ or 2% $O_2$), all in nitrogen carrier gas. FIGS. 5 and 6 compare the subtracted thermographic responses of the semiconductor compositional arrays at 450° C. and 600° C., respectively, with an applied bias of 10 V for the gases 2000 ppm CO in $N_2$, 2000 ppm $NO_x$ in $N_2$, 2000 ppm $NO_x$/2% $O_2$ in $N_2$, and $N_2$ relative to a 2% $O_2$/98% $N_2$ reference gas. For n-type semiconductors (e.g., ZnO, $AlVO_4$, $SnO_2$, $WO_3$), the donor gas CO added electrons to the conduction band, reducing the resistance and increasing the current flow relative to the materials which are unaffected by CO (e.g., $BaTiO_3$, $CaTiO_3$, the $Al_2O_3$ blank, $SrNb_2O_6$). This increased current dominated the $I^2R$ heating and was detected as an increase in temperature. On the other hand, the acceptor gas $NO_x$ removed electrons from the conduction band and reduced the current relative to materials unaffected by $NO_x$. This decrease in current was detected as a relative cooling of the $NO_x$-sensitive materials (ZnO, $AlVO_4$, $SnO_2$, $WO_3$). Likewise, 2000 ppm $NO_x$/2% $O_2$ in $N_2$ behaved as an acceptor gas and $N_2$ behaved as a donor gas relative to the 2% $O_2$/98% $N_2$ reference gas.

Conversely, the addition of electrons to a p-type semiconductor's valence band increased the resistance and reduced the current flow. This decrease in current was detected as a relative cooling of the CO-sensitive p-type materials (CuO, $SrTiO_3$, $Cu_2O$, NiO). The images demonstrate the utility of voltage bias-enhanced thermography as a screening tool for both n- and p-type semiconductor sensitivity to various gas mixtures.

Figure 7:
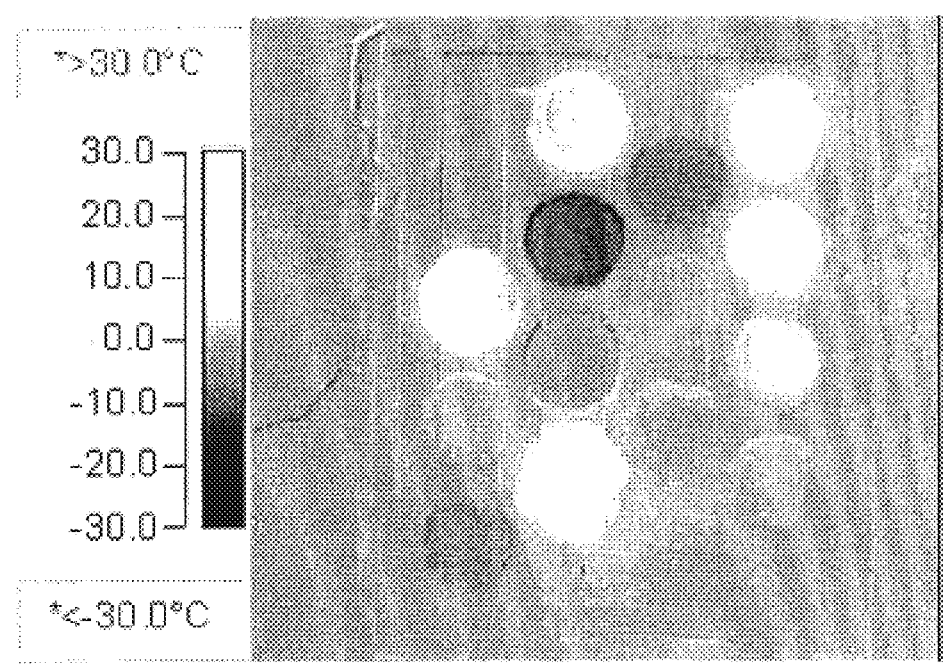
FIG. 7 is the thermographic images of a sample array exposed to butane at 450° C.

FIG. 7 compares the subtracted thermographic responses of the semiconductor compositional array at 450° C. with an applied bias of 10 V for 1% butane in $N_2$ relative to a 2% $O_2$/98% $N_2$ reference gas. The donor gas butane added electrons to the n-type semiconductor's conduction band (ZnO, $AlVO_4$, $SnO_2$, $WO_3$), reducing the resistance and increasing the current flow relative to the materials which are unaffected by butane (e.g., $BaTiO_3$, $CaTiO_3$, the $Al_2O_3$ blank, $SrNb_2O_6$). This increased current dominates the $I^2R$ heating and was detected as an increase in temperature. Conversely, for the p-type semiconductor materials (CuO, $SrTiO_3$, $Cu_2O$, NiO), butane added electrons to the valence band and reduced the current relative to materials unaffected by butane. This decrease in current was detected as a relative cooling of the p-type materials.

The images demonstrate the utility of voltage bias-enhanced thermography as a screening tool for semiconductor sensitivity to various gas mixtures as well as the use of this technique for determining p-type or n-type conductivity of semiconductors.

Example 3
Effect of Surface Area

The first four pads of the sensor array depicted in FIG. 3 contain ZnO fired to different temperatures. With increasing processing temperature, the surface area of the ZnO decreased (ZnO standard—7.0 $m^2$/g, ZnO (750° C.) 4.1 m$^2$/g, ZnO (1000° C.)—0.8 m$^2$/g, ZnO (1250° C.)—0.2 m$^2$/g) as measured by BET analysis. Since the quantity of CO gas adsorption by a particular ZnO sample is related to its surface area, the thermal signal correlated with the surface area for CO, as seen in FIG. 5.

Example 4
Effect of Temperature

Figure 8:
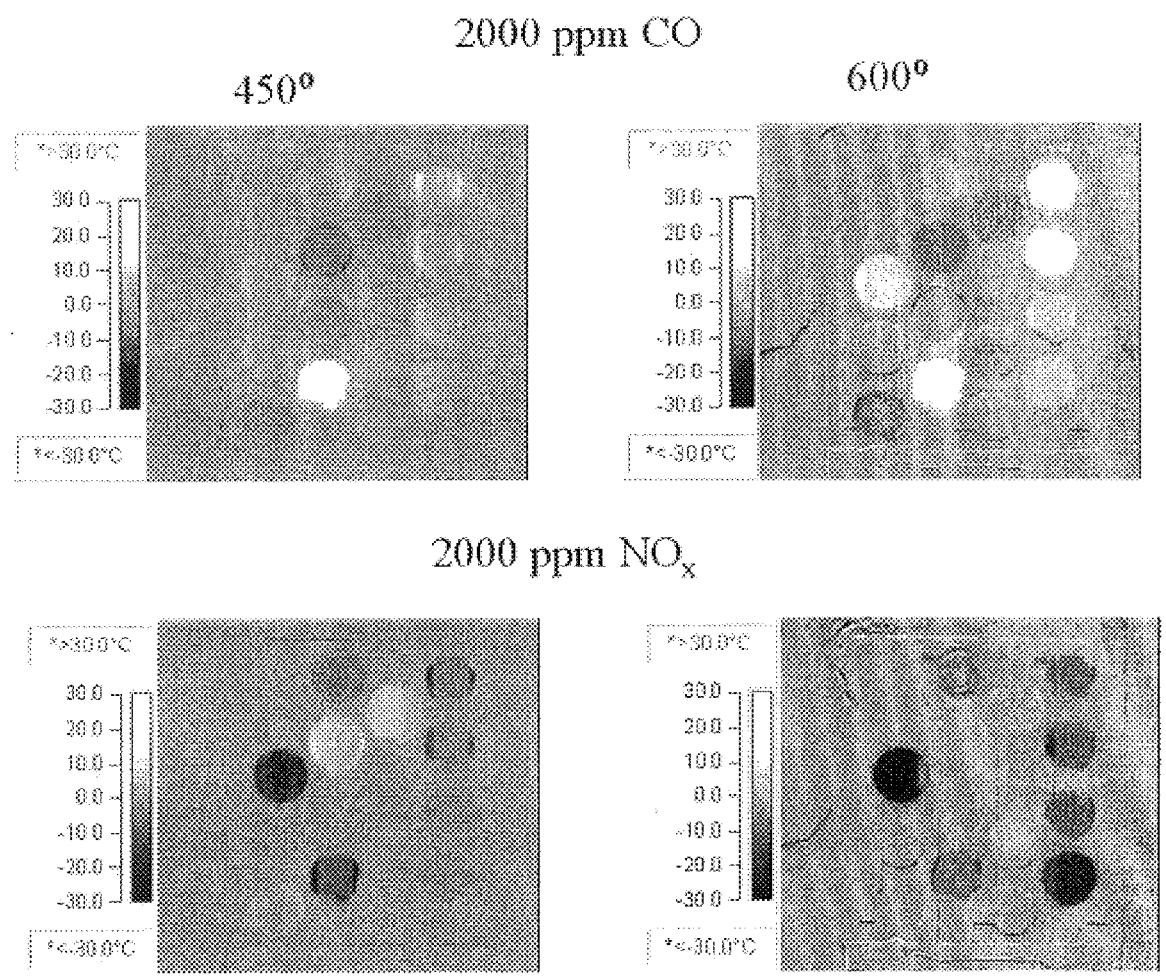
FIG. 8 is the thermographic images of a sample array exposed to CO and $NO_x$ at 400° C. and at 600° C.

FIG. 8 depicts the response of the sensor pads to CO and NO$_x$ at 10V bias for both 450 and 600° C. For most semiconductors the observed thermal response intensifies with the temperature increase in CO due to a general decrease in resistivity of semiconductors with increasing temperature. The decrease in resistivity allows for an increase in current flow through the sensor pad. Therefore, the thermal signal intensifies since it is dominated by the squared term of the I$^2$R heating. However, in certain instances the observed signal changes uncharacteristically. In NO$_x$, in particular, while the thermal signals for n-type WO$_3$ and ZnO increase at the higher temperature, the n-type signal for SnO$_2$ and AlVO$_4$ decreases and the p-type signal for both NiO and Cu$_2$O disappears completely. Thus it can be seen that the sensitivity of a particular material to a particular gas can be strongly temperature-dependent.

Example 5
Effect of Sample Thickness

Figure 9:
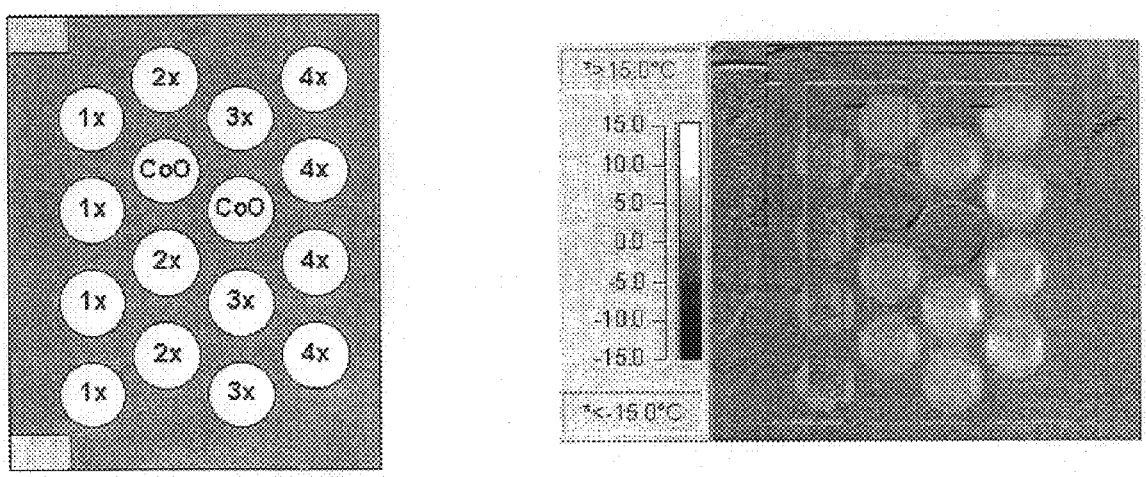
FIG. 9 is the compositional map and thermographic images of a sample array of various thicknesses of ZnO.

A sample array containing varying thicknesses of ZnO was prepared. The increase in thickness of the pads was accomplished by multiple screen-printings of ZnO into each well. Prior to ZnO addition, two wells (#'s 6 and 10) were masked off to allow for the addition of two pads of the emissivity standard CoO. Then a second screen printing was performed on wells 1–12; a third on wells 1–8; and a fourth on wells 1–4. FIG. 9 shows the compositional map and subtracted image of the thermal response of the various thicknesses of ZnO to 2000 ppm of CO in N$_2$ at 7 volts bias and 450° C. The thermal response at a particular thickness was uniform, and as sample thickness increased the thermal signal increased. However above three thicknesses the signal tended to saturate. Thus for hand painted samples, where the thickness of the sample is typically much greater than for screen-printed samples, a maximum signal would be seen.

What is claimed is:

1. A method for determining the change in the resistance of a semiconducting material in response to exposure to a sample gas, comprising the steps of:
    a) applying a voltage bias across the semiconducting material;
    b) measuring the difference between the temperature of the material as exposed to the sample gas and the temperature of the material as exposed to a reference gas; and
    c) relating the measured difference in temperature to a change in the resistance of the semiconducting material.

2. The method as in claim 1 wherein the voltage bias is about 0.5V to about 200V.

3. The method as in claim 1 wherein the difference in the temperature is measured with an infrared thermographic measuring system.

4. The method as in claim 1 wherein the semiconducting material comprises a metal oxide.

5. The method as in claim 4 wherein the semiconducting material is deposited on a solid substrate.

6. A method for the parallel screening of a plurality of semiconducting materials for suitability as chemical sensing materials, comprising the steps of:
    a) applying a voltage bias across each semiconducting material;
    b) simultaneously measuring the difference between the temperature of each material as exposed to a sample gas and the temperature of each material as exposed to a reference gas; and
    c) comparing the measured difference in temperature exhibited by a first material to the measured difference in temperature exhibited by a second material.

7. The method as in claim 6 wherein the voltage bias is about 0.5V to about 200V.

8. The method as in claim 6 wherein the difference in the temperature is measured with an infrared thermographic measuring system.

9. The method as in claim 6 wherein the semiconducting material comprises a metal oxide.

10. The method as in claim 6 wherein the semiconducting material is deposited on a solid substrate.

11. A method for determining the conductivity type of a semiconducting material, comprising:
    a) applying a voltage bias across the semiconducting material;
    b) measuring the difference between the temperature of the material as exposed to a sample gas and the temperature of the material as exposed to a reference gas; and
    c) relating the measured difference in temperature to a conductivity type.

12. The method as in claim 11 wherein the sample gas or the reference gas is a donor gas.

13. The method as in claim 11 wherein the sample gas or the reference gas is an acceptor gas.

14. The method as in claim 11 wherein the voltage bias is about 0.5V to about 200V.

15. The method as in claim 11 wherein the difference in the temperature is measured with an infrared thermographic measuring system.

16. The method as in claim 11 wherein the semiconducting material comprises a metal oxide.

17. The method as in claim 11 wherein the semiconducting material is deposited on a solid substrate.

* * * * *